| United States Patent [19] | [11] Patent Number: 4,843,071 |
| Hohenwarter | [45] Date of Patent: Jun. 27, 1989 |

[54] METHOD AND COMPOSITION FOR TREATING OBESITY, DRUG ABUSE, AND NARCOLEPSY

[75] Inventor: Mark Hohenwarter, Mobile, Ala.

[73] Assignee: Serotonin Industries of Charleston, Charleston, S.C.

[21] Appl. No.: 938,307

[22] Filed: Dec. 5, 1986

[51] Int. Cl.$^4$ .................. A61K 31/55; A61K 31/435; A61K 31/44

[52] U.S. Cl. .................................. 514/217; 514/277; 514/345; 514/474; 514/656; 514/810; 514/909; 514/953; 514/966; 514/967; 424/422; 424/465; 424/DIG. 15

[58] Field of Search ............... 514/217, 656, 474, 272, 514/345, 810, 909, 966, 967, 953; 424/465, 422, DIG. 15

[56] References Cited

U.S. PATENT DOCUMENTS

| 3,961,060 | 6/1976 | Fuxe | 514/217 |
| 4,470,987 | 9/1984 | Wurtman | 514/314 |
| 4,598,094 | 7/1986 | Wurtman | 514/561 |

FOREIGN PATENT DOCUMENTS 1239345 7/1971 United Kingdom .

OTHER PUBLICATIONS

The Merck Index, 9th ed., p. 1262, Nos. 9493 & 9494.
Goodman & Gilman, The Pharm. Basis of Theropeutics, 6th ed., 1980, pp. 1570, 71, 1577 and 1578.
Wurtman et al., *Science*, 185:183-184 (1974).
Giannini, A. J. et al., *J. Clin. Pharmacol.*, 26:211-214 (1986).
Menon, M. K. et al., *Eur. J. Pharmacol.*, 12:156-160 (1970).
Miller, S. C. et al., *Neuropsychobiology* 13:160-166 (1985).

*Primary Examiner*—John W. Rollins
*Attorney, Agent, or Firm*—Saidman, Sterne, Kessler & Goldstein

[57] ABSTRACT

Compositions and methods are disclosed for the treatment of obesity, depression, drug abuse, and narcolepsy. The compositions comprise a norepinephrine precursor such as L-tyrosine or L-phenylalanine in combination with a norepinephrine re-uptake inhibitor such as desipramine. In another embodiment of the invention, the compositions further comprise enzymatic cofactors for the biosynthesis of norepinephrine.

27 Claims, No Drawings

METHOD AND COMPOSITION FOR TREATING OBESITY, DRUG ABUSE, AND NARCOLEPSY

FIELD OF THE INVENTION

This invention relates to compositions comprising a norepinephrine precursor, such as L-tyrosine or L-phenylalanine in combination with a norepinephrine re-uptake inhibitor such as desipramine. The compositions are useful in controlling obesity, depression, drug abuse, and narcolepsy in animals. The invention also relates to said compositions further comprising one or more enzymatic cofactors for the biosynthesis of norepinephrine. This invention further relates to a method of controlling obesity, depression, drug abuse, or narcolepsy in an animal comprising administering an effective amount of the compositions of this invention to said animal.

BACKGROUND OF THE INVENTION

The use of appetite supressants such as diethylproprion and phenylpropanolamine operate by directly and/or indirectly stimulating noradrenergic receptors in the brain. However, long-term use of these drugs is met with increasing tolerance in most patients, requiring increased dosage and more frequent administration to achieve continued appetite suppression. Tolerance to these products occurs as the result of a depletion of norepinephrine from storage sites in the neuron with the use of indirect-acting agents.

Catecholamines are stored in subcellular granules and released by exocytosis in the adrenal medulla and sympathetic nerve endings. The biosynthesis of catecholamines proceeds from the amino acid phenylalanine which is sequentially hydroxylated to form tyrosine, then 3,4-dihydroxyphenylalanine (DOPA). DOPA is decarboxylated to form dopamine. Hydroxylation on the beta position of the side chain forms norepinephrine.

The initial step, the hydroxylation of tyrosine, was believed to be rate-limited and regulated so that synthesis was coupled to release. This regulation has been thought to be achieved by alterations in both the activity and the amount of tyrosine hydroxylase. Harrison's *Principles of Internal Medicine*, 10th edition, edited by Petersdorf, R. G. et al, page 410 (1983).

After release by exocytosis, much of the norepinephrine is recaptured by an active reuptake mechanism. Additionally, norepinephrine is metabolized by O-methylation of the meta-hydroxyl group and oxidative deamination. O-Methylation is catalyzed by the enzyme catechol-O-methyltransferase (COMT). Oxidative deamination is promoted by monoamine oxidase (MAO). MAO is important in regulating the catecholamine stores within the peripheral sympathetic nerve endings. For a more complete description of the biosynthesis and metabolism of the catecholamines, see Harrison, supra, pages 409–412.

The pyridoxines are a group of B6 vitamins which include pyridoxine, pyridoxal, and pyridoxamine and their five-phosphate esters. The coenzyme formed in vivo is pyridoxal-5-phosphate. The compounds owe their enzymatic activity to conversion in vivo to pyridoxal-5-phosphate. Pyridoxal-5-phosphate acts as a cofactor for a large number of enzymes involved in amino acid metabolism, including transaminases, synthetases, and hydroxylases, and is a known enzyme cofactor in the biosynthesis of norepinephrine from phenylalanine and tyrosine. Ascorbic acid plays a role as an enzymatic cofactor in hydroxylation reactions. Accordingly, ascorbic acid participates in the biosynthesis of DOPA from tyrosine and in the biosynthesis of norepinephrine from dopamine. Goodman and Gilman's, *The Pharmacological Basis of Therapeutics*, 7th Edition, edited by Gilman, A. G. et al, Macmillan Publishing Company, New York, N.Y. (1985) pp. 82, 1559–1560.

Contrary to the idea that brain catecholamine levels cannot be effectively raised by tyrosine administration, it has been observed that increasing brain tyrosine levels does increase brain DOPA levels. Conversely, decreases in brain DOPA levels could be produced in rats by decreasing brain tyrosine levels. Wurtman et al., *Science* 185:183–184 (1974). Increased brain levels of tyrosine were achieved by administering tyrosine itself.

U.S. Pat. No. 4,470,987 to Wurtman et al., discloses a composition for reducing the risk of ventricular fibrilation in animals by administering tyrosine or a tyrosine precursor, either alone or in combination with a further substance known to reduce the risk of ventricular fibrillation. According to the disclosure, increased synaptic norepinephrine levels are obtained by administering tyrosine. Wurtman also discloses that phenylalanine can, in low doses, be used in place of tyrosine Phenylalanine and tyrosine act by increasing the release of catecholamines (dopamine, norepinephrine, or epinephrine) into synapses which in turn reduce the firing frequency of the sympathetic neurons running to the heart, thereby decreasing cardiac excitability and vulnerability.

U.S. Pat. No. 4,598,094, to Wurtman, discloses the concomitant administration of tyrosine with an indirect-acting sympathomimetic drug to increase the level of norepinephrine released in the sympathetic neuron synapses. The claimed invention is a composition and a process for preventing tachyphylaxis, caused by amphetamine administration, comprising concomitantly administering amphetamine with a catecholamine precursor such as L-tyrosine. L-tyrosine serves to replete norepinephrine which had been depleted by the indirect acting sympathomimetic drugs.

Desipramine is a member of the tricyclic family of antidepressants, which block the presynaptic re-uptake of norepinephrine in the central nervous system. Other tricyclic antidepressants include imipramine hydrochloride, imipramine pamoate, amitriptyline hydrochloride, and protriptyline hydrochloride. These compounds have anti-anxiety and sedative properties which make them useful in the treatment of mild depression. See Remington's *Pharmaceutical Sciences*, edited by R. Osol, Mack Publishing Company, Easton, Pa., page 1038 (1980).

Desipramine has been reported to be effective in decreasing depressive symptoms of phencyclidine and cocaine abusers. Phencyclidine and cocaine have been shown to release dopamine and norepinephrine presynaptically and are equipotent to amphetamine in blocking catecholamine reuptake. Giannini, A. J., et al., *J. Clin. Pharmacol.* 26:211–214 (1986). The authors hypothesize that the tricyclic antidepressants are effective in treating cocaine abuse due to the induction of receptor subsensitivity. The suggestion that desipramine is effective in PCP withdrawal because of its ability to block reuptake of norepinephrine was not supported by their findings. Re-uptake blockade is felt to occur rather quickly, whereas alteration of receptors occurs after three to four weeks. The authors report that a two-week time period after starting desipramine was necessary in order to obtain the therapeutic effect in both cocaine and PCP abusers.

Desipramine has also been reported to enhance the anorectic effects of d-amphetamine, phentermine, and diethylpropion, but did not modify those of phenmetrazine and chlorphentermine. Menon, M. K., et al., *Eur. J. Pharmacol.* 12:156–160 (1970). The authors hypothesize that potentiation and prolongation of the effects of d-amphetamine, phentermine, and diethylpropion by desipramine are probably due to interference with their metabolism, leading to an increase in the half-life of the substances in the body.

The clinical effect of desipramine and imipramine in depressed patients has been found to be related to the plasma ratios of tryptophan and tyrosine to competing amino acids. Miller, S. E., et al., *Neuropsychobiology* 13:160–166 (1985). The authors concluded that determination of pretreatment plasma ratios of tryptophan and tyrosine to competing amino acids may serve as a useful and convenient direction for the adjustment of serum imipramine and desipramine to optimal therapeutic levels in individual depressives.

Thus, a medicament comprising the combination of a norepinephrine precursor and a norepinephrine re-uptake inhibitor, said medicament useful for the treatment of obesity, depression, drug abuse, or narcolepsy is not taught or suggested by the prior art.

SUMMARY OF THE INVENTION

This invention relates to methods and compositions for the treatment of obesity, depression, drug abuse, and narcolepsy. The compositions comprise a norepinephrine precursor such as L-tyrosine or L-phenylalanine in combination with a norepinephrine re-uptake inhibitor such as desipramine. The compositions may further comprise an effective amount of enzymatic cofactors for the biosynthesis of norepinephrine.

The invention relates as well to the use of these compositions in the treatment of obesity, depression, drug abuse, and narcolepsy in an animal. Treatment comprises administration of a norepinephrine precursor in combination with a norepinephrine re-uptake inhibitor, optionally with enzymatic cofactors for the biosynthesis of norepinephrine, to the animal in amounts effective to treat obesity, depression, drug abuse, and narcolepsy.

In response to the longstanding need for treating obesity, depression, drug abuse, and narcolepsy, the present invention was developed. The objective of this invention is to increase the synthesis of brain norepinephrine to normal to supranormal levels by administering a norepinephrine precursor and then to maintain this therapeutic concentration at the synaptic cleft by blocking its re-uptake into the presynaptic nerve terminus by co-administration of a norepinephrine re-uptake inhibitor. A further objective of this invention comprises the co-administration of enzyme co-factors in the biosynthetic pathway for in vivo norepinephrine biosynthesis.

The method of controlling obesity, depression, drug abuse, or narcolepsy comprises administering the composition of this invention to an animal.

DESCRIPTION OF THE PREFERRED EMBODIMENT

By the term "norepinephrine precursor" is intended L-tyrosine, L-phenylalanine, and the pharmaceutically acceptable salts of L-tyrosine and L-phenylalanine.

L-phenylalanine is an essential component in human nutrition, not synthesized by the human body. Methods for its preparation include synthesis from L-tyrosine. Coffey et al. *J. Chem. Soc.* 1400 (1959); Viswanatha, V. et al. *J. Org. Chem.* 45:2010 (1980). L-Phenylalanine is isolated commerically from proteins such as oval-albumin, lactalbumin, zein and fibrin See *The Merck Index*, edited by Martha Windholz, Merck & Company, Inc., Rahway, New Jersey, page 7144 (1983).

L-Tyrosine is a widely distributed amino acid, classified as nonessential in respect to the growth effect in rats. See *The Merck Index*, supra page 1406. L-Tyrosine is a natural product which can be isolated from silk waste (Abder Halem et al., *D. Phyiol. Chem.* 48:528 (1906), from casein (Marshal, *J. Biol. Chem.* 15:85 (1913), and from corn (U.S. Pat. No. 2,178,210 (1940)).

By the term "norepinephrine re-uptake inhibitor" is intended compounds which block the re-uptake of norepinephrine into the presynaptic nerve terminus Norepinephrine re-uptake inhibitors include, but are not limited to, desipramine, imipramine, amoxapine, nortriptyline, protriptyline, and maprotiline and pharmaceutically acceptable salts thereof. Methods of preparation of desipramine hydrochloride are described in Belgium Pat. No. 614,616 (C.A. 58:11338C (1963)). Preparation of the free base and hydrochloride is disclosed in British Pat. No. 908,788 (1962).

The preparation of amoxapine, a known antidepressant, is reported by Schmultz, J., et al., *Helv. Chim. Acta* 15:245 (1967). The preparation of nortriptyline, another known antidepressant, is reported by Hoffsommer et al., *J. Org. Chem.* 27:4134 (1962). A comprehensive description of nortriptyline is provided by Hale, J. L., in *Analytical Profiles of Drug Substances*, Volume 1, K. Florey, Ed. (Academic Press, New York, 1972), pp. 233–247. The synthesis of the antidepressant protriptyline is described in U.S. Pat. Nos. 3,244,748 and 3,271,451, and in Belgium Patent No. 617,967. Protriptyline has also been reported to be useful in treatment of sleep apnea (Clark, R. W., et al., *Neurology* 29:1287 (1979); Brownell, L. G., et al., *N. England J. Med.* 307:1037 (1982)). Preparation of the antidepressant maprotiline is reported in Swiss Pat. Nos. 467,237 and 467,747, and in Wilhelm et al., *Helv. Chim. Acta* 52:1385 (1969).

By the term "animal" is intended all animals in which norepinephrine is manufactured biosynthetically and for which the re-uptake of norepinephrine at the synaptic cleft can be blocked. Foremost among such animals are humans; however, the invention is not intended to be so limiting, it being within the contemplation of the invention to treat any and all animals which may experience the beneficial effects of the invention.

By the term "pyridoxine" is intended not a single substance but rather a group of naturally occurring pyridines that are metabolically and functionally interrelated. These included pyridoxine, pyridoxal, and pyridoxamine and the pharmaceutically acceptable salts thereof, such as pyridoxine hydrochloride. The synthesis of pyridoxine hydrochloride is described in U.S. Pat. Nos. 2,680,743; 2,734,063; 2,904,551; and 3,024,244, incorporated by reference herein.

By the term "ascorbic acid" is intended ascorbic acid, and the synthetic and natural analogs of ascorbic acid, which can be converted to the active form in vivo, and the pharmaceutically acceptable salts thereof. A synthetic procedure for producing ascorbic acid is described in U.S. Pat. No. 2,702,808 incorporated by reference herein.

By the term "pharmaceutically acceptable salts" is intended salts with pharmaceutically acceptable acids or bases, e.g., acids such as sulphuric, hydrochloric, nitric, phosphoric acid, etc., or bases such as alkali or alkaline earth metal hydroxides, ammonium hydroxides, alkylammonium hydroxides, etc.

By the term "supranormal levels" is intended levels of norepinephrine in excess of those normally found as a result of the body's natural production of norepinephrine or the levels induced by the administration of a norepinephrine re-uptake inhibitor or a norepinephrine precursor alone.

By the term "co-administrated" is intended that each of at least two compounds will be administered during a time frame wherein the respective periods of pharmacological activity overlap.

The compositions of the present invention comprise a norepinephrine precursor in combination with a norepinephrine re-uptake inhibitor. The composition may further comprise amounts of one or more enzymatic cofactors effective for the biosynthesis of norepinephrine or the pharmaceutically acceptable salts thereof.

Tyrosine is formed in vivo from phenylalanine by a hydroxylation reaction catalyzed by phenylalanine hydroxylase, which requires NADPH as coreductant and dihydrobiopterin as cofactor. See Lehninger, A. L. *Biochemistry*, Worth Publishers, New York, N.Y. (1970), pp. 542. Ascorbic acid is involved in the synthesis of norepinephrine by facilitating the hydroxylation of tyrosine to form DOPA, and the hydroxylation of dopamine to form norepinephrine. The decarboxylation of DOPA to give dopamine involves a pyridoxine catalyzed enzymatic reaction. Thus, the addition of at least one of pyridoxine and ascorbic acid, in an amount effective to cofactor the biosynthesis of norepinephrine from its precursor, to the composition containing a norepinephrine precursor and a norepinephrine re-uptake inhibitor, ensures that a predictable maximum biosynthesis of norepinephrine will result in all all animals being treated, regardless of their individual nutritional status.

Compositions within the scope of this invention include all compositions wherein each of the components thereof is contained in an amount effective to achieve its intended purpose. Thus, the compositions contain one or more norepinephrine precursors in an amount sufficient to result, upon administration, in the biosynthesis of normal to supranormal levels of norepinephrine.

Similarly, the compositions contain one or more norepinephrine re-uptake inhibitors in an amount sufficient to inhibit the re-uptake of norepinephrine at the synapse. Further, where the precursor and inhibitor are co-administered separate and apart from one another, the same criteria for determining levels of administration apply. While individual needs vary, determination of optimal ranges of effective amounts of each component is within the skill of the art.

Typical unit dosage forms contain 125–2000 mg of a norepinephrine precursor or an equivalent amount of the pharmaceutically acceptable salt thereof, 10–75 mg of the norepinephrine re-uptake inhibitor or an equivalent of the pharmaceutically acceptable salt thereof, and, where present, 10–100 mg of pyridoxine or an equivalent amount of the pharmaceutically acceptable salt of pyridoxine, and 50–500 mg of ascorbic acid or an equivalent amount of the pharmaceutically acceptable salt of ascorbic acid.

Typical compositions of the present invention contain, per part by weight of the norepinephrine re-uptake inhibitor or an equivalent amount of the pharmaceutically acceptable salt thereof, 0.5 to 500, preferably 2 to 200, parts by weight of the norepinephrine precursor or an equivalent amount of the pharmaceutically acceptable salt thereof, and, if present, 0.02–4 parts by weight of pyridoxine or an equivalent amount of a pharmaceutically acceptable salt of pyridoxine, and 0.4–20 parts by weight of ascorbic acid or an equivalent amount of a pharmaceutically acceptable salt of ascorbic acid.

In addition to the pharmacologically active compounds, the new pharmaceutical preparations may contain suitable pharmaceutically acceptable carriers comprising excipients and auxilliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.1 to 99 percent, preferably from about 25–85 percent of active compound(s), together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding a resulting mixture and processing the mixture of granules, after adding suitable auxilliaries, if desired or necessary, to obtain tablets or dragee cores.

Suitable excipients are, in particular, fillers such as sugars, for example lactose or sucrose, mannitol or sorbitol, cellulose preparations and/or calcium phosphates, for example tricalcium phosphate or calcium hydrogen phosphate, as well as binders such as starch, paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or algenic acid or a salt thereof, such as sodium alginate. Auxiliaries are, above all, flow-regulating agents and lubricants, for example, silica, talc, steric acid or salts thereof, such as magnesium stearate or calcium stearate, and/or polyethylene glycol. Dragee cores are provided with suitable coatings which, if desired, are resistant to gastric juices. For this purpose, concentrated sugar solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxy- propylmethyl-cellulose phthalate, are used. Dye stuffs or pigments may be added to the tablets or dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Possible pharmaceutical preparations which can be used rectally include, for example, suppositories, which consist of a combination of the active compounds with a suppository base. Suitable suppository bases are, for example, natural or synthetic triglycerides, paraffin hydrocarbons, polyethylene glycols or higher alkanols. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension include, for example, sodium carboxymethyl cellulose, sorbitol, and/or dextran. Optionally, the suspension may also contain stabilizers.

The compositions of the present invention, in and of themselves, find utility for appetite suppression. One postulate for appetite suppression is related to mediation via noradrenergic stimulation. Many prescription (e.g., diethylproprion) and over-the-counter (e.g., phenylpropanolamine) products currently marketed indirectly and/or directly stimulate noradrenergic (norepinephrine) receptors and thus suppress appetite. Tolerance to these products can occur, however, because of depletion of norepinephrine from storage sites in the neuron which occurs with the use of indirect acting agents. The unique mechanism of action of this invention results in appetite suppression with minimal tolerance potential.

Further, it has also been found that the compositions are useful in treatment of depressive illnesses associated with norepinephrine depletion. The combination of a norepinephrine precursor and a norepinephrine re-uptake inhibitor repletes norepinephrine stores and corrects the underlying biochemical condition which causes the depression.

Further, it has also been found that the compositions of the present invention are useful in the treatment of the side effects that result from drug abuse of stimulant agents (cocaine, amphetamines, phencyclidine). Drug abuse to cocaine, amphetamine, phencyclidine, and other CNS stimulants result in depletion of norepinephrine stores, and in some cases, reductions in plasma tyrosine levels. Treatment of drug abuse with desipramine alone requires a two-to- three-week waiting period before the onset of action.

Giannini, A. J., et al., *J. Clin. Pharmacol.* 26:211–214 (1986). The composition of this invention is useful in treating depression and the craving symptoms of drug abuse by acting more quickly than desipramine alone, with greater efficacy.

Further, it has also been found that the compositions of the present invention are useful for the treatment of narcolepsy. Narcolepsy is associated with depletion of brain catecholamines. The composition of the present invention serves to replete norepinephrine stores and relieve the symptoms of narcolepsy.

The composition of the present invention may be administered by any means that affects appetite suppression, antidepression, control of drug abuse, or narcolepsy. For example, administration may be parenterally, subcutaneously, intravenously, intramuscularly, or intraperitoneally. Alternatively, or concurrently, administration can be by the oral route. The dosage administered will be dependant upon the age, health, and weight of the recipient, kind of concurrent treatment, if any, frequency of treatment, and the nature of the effect desired.

Administration of the composition is desirably effected in from one to eight dosage units daily, depending on the mode of administration, preferably by oral administration, e.g., liquids, capsules, or tablets. Each dosage contains 125–2000 mg (1–16 gram per day) of the norepinephrine precursor, 10–75 mg (80–600 mg per day) of the norepinephrine re-uptake inhibitor, 10–100 mg (80–800 mg per day) of pyridoxine, if present, and 50–500 mg (400–4000 mg per day) of ascorbic acid, if present.

The following examples are illustrative, but not limiting, of the method and composition of the present invention. Other suitable modifications and adaptations of the variety of conditions and parameters normally encountered in clinical therapy and which are obvious to those skilled in the art are within the spirit and scope of this invention.

EXAMPLE 1

The patient was a thirty year old white female (5'10", 151 lbs.). A licensed physician initiated desipramine (25 mg) and L-tyrosine (1 gm) therapy beginning Sept. 10, 1986. The patient was six months post-partum and desired to attain her pre-pregnancy weight of 145 lbs. Before initiation of therapy, she was unable to lose this desired five to ten pounds, despite voluntary attempts at controlling appetite. She daily self-administered 1 dose of desipramine/L-tyrosine orally, every morning from Sept. 10, 1986 to Oct. 1, 1986. She did not advance the daily dose beyond the initial starting regimen of desipramine (25 mg) and L-tyrosine (1 gm). During this period of treatment, she reported a marked decrease in appetite and lost a total of seven pounds. Weight loss was achieved during therapy as follows:

| Date | Patient's Weight |
| --- | --- |
| September 10, 1986 | 151 lbs. |
| September 16, 1986 | 148 lbs. |
| September 24, 1986 | 146 lbs. |
| October 1, 1986 | 144 lbs. |

Therapy was discontinued Oct. 1, 1986 as the patient reached her desired weight loss goal.

EXAMPLE 2

A thirty year old white male (6' 6", 223 lbs.) had gradually increased in weight from approximately 205 lbs. to his current weight of 223 lbs. over the prior two years. Under the supervision of a licensed physician, therapy for appetite suppression was initiated (desipramine 25 mg, L-tyrosine 1 gm, 1 dose/day) every morning beginning Sept. 2, 1986 until Sept. 30, 1986. Desipramine/L-tyrosine therapy was administered via the oral route with the desipramine in tablet form and the L-tyrosine in capsule form. Upon initiating therapy, the patient's appetite subjectively decreased with a corresponding decrease in caloric consumption. The patient exhibited a fifteen pound weight loss during the ensuing four week period while receiving desipramine/L-tyrosine therapy. The patient was weighed prior to initiating therapy and twice weekly during therapy. Weight loss was achieved during therapy as follows:

| Date | Patient's Weight |
|---|---|
| September 2, 1986 | 223 lbs. |
| September 5, 1986 | 221 lbs. |
| September 9, 1986 | 220 lbs. |
| September 12, 1986 | 218 lbs. |
| September 16, 1986 | 215 lbs. |
| September 19, 1986 | 214 lbs. |
| September 23, 1986 | 212 lbs. |
| September 26, 1986 | 210 lbs. |
| September 30, 1986 | 208 lbs. |

Therapy was discontinued Sept. 30, 1986 upon patient's request as the goal of therapy was obtained

EXAMPLE 3

A thirty-one year old white male (6' 0", 175 lbs.) had recently dieted and most recently (May 1986) weighed 191 pounds three months prior to initiating therapy. This patient did particularly well in losing weight over a two month period beginning in May 1986, after which his weight stabilized at 175 pounds. His goal was to achieve his ideal body weight of 170 pounds. He continued his voluntary efforts to lose additional weight but after a one month period was unsuccessful in achieving this.

Starting on Aug. 28, 1986 the patient self-administered a desipramine tablet (25 mg) and a L-tyrosine capsule (1 gm) orally every morning. He continued therapy until Oct. 2, 1986 at this same dosage regimen except from Sept. 2, 1986 until Sept. 19, 1986 when he self administered desipramine (25 mg) and L-tyrosine (1 gm) orally twice a day. During the total timespan, he reported a strong appetite suppressant effect and lost a total of five pounds. Weight loss was achieved during therapy as follows:

| Date | Patient's Weight |
|---|---|
| August 28, 1986 | 175 lbs. |
| September 4, 1986 | 173 lbs. |
| September 11, 1986 | 173 lbs. |
| September 18, 1986 | 172 lbs. |
| September 25, 1986 | 172 lbs. |
| October 2, 1986 | 170 lbs. |

Therapy was discontinued Oct. 2, 1986 as the patient reached his desired weight loss goal.

EXAMPLE 4

A 53 year old white female (5'3, 175 lbs.) under the supervision of a licensed physician was prescribed desipramine (25 mg tablets) and L-tyrosine (1 gm capsules); one of each to be taken every morning for appetite suppression. Therapy began Sept. 3, 1986 and continued to Sept. 24, 1986. During this timeframe, the patient described a definite appetite suppressant effect. She recorded daily intakes of food which were below what she had taken prior to therapy. Her weight decreased from 175 pounds to 165 pounds during therapy. Weight loss during therapy was as follows:

| Date | Patient's Weight |
|---|---|
| September 3, 1986 | 175 lbs. |
| September 7, 1986 | 172 lbs. |
| September 13, 1986 | 168 lbs. |
| September 20, 1986 | 165 lbs. |
| September 24, 1986 | 165 lbs. |

Having now fully described this invention, it will be appreciated by those skilled in the art that the same can be performed within a wide range of equivalent parameters of composition, conditions, and modes of administration without departing from the spirit or scope of the invention or any embodiment thereof.

What is claimed is:

1. A composition useful for the treatment of obesity, drug abuse and narcolepsy comprising effective amount of:
   a. a norepinephrine precursor; and
   b. a norepinephrine re-uptake inhibitor.

2. The composition of claim 1 further comprising an effective amount of one or more enzymatic cofactors for the biosynthesis of norepinephrine.

3. The composition of claims 1 or 2 and a pharmaceutically acceptable carrier.

4. The composition of claim 3 in the form of a liquid, a suspension, a tablet, a dragee, an injectable solution, or a suppository.

5. The composition of claim 2 wherein the enzymatic cofactors include at least one of pyridoxine, ascorbic acid, or the pharmaceutically acceptable salts thereof in an amount, effective to enzymatically cofactor biosynthesis of norepinephrine.

6. The composition of claim 1 wherein the norepinephrine precursor is selected from the group consisting of L-tyrosine and L-phenylalanine, or the pharmaceutically acceptable salts thereof.

7. The composition of claim 6 wherein the norepinephrine precursor is L-tyrosine.

8. The composition of claim 1 wherein the norephinephrine re-uptake inhibitor is selected from the group consisting of desipramine, imipramine, amoxapine, nortriptyline, protriptyline, and maprotiline, or the pharmaceutically acceptable salts thereof.

9. The composition of claim 8 wherein the norepinephrine re-uptake inhibitor is desipramine.

10. The composition of claim 1 comprising, per part by weight of the norepinephrine re-uptake inhibitor or an equivalent amount of the pharmaceutically acceptable salt of said norepinephrine re-uptake inhibitor, 0.5–500 parts by weight of said norepinephrine precursor or an equivalent amount of the pharmaceutically acceptable salt of said norepinephrine precursor.

11. The composition of claim 5 comprising, per part by weight of the norepinephrine re-uptake inhibitor or an equivalent amount of the pharmaceutically acceptable salt of said norepinephrine re-uptake inhibitor, 0.5–500 parts by weight of said norepinephrine precursor, or an equivalent amount of the pharmaceutically acceptable salt of said norepinephrine precursor, 0.05–4 parts by weight of pyridoxine or an equivalent amount of a pharmaceutically acceptable salt of pyridoxine, and 0.4–20 parts by weight of said ascorbic acid or an equivalent amount of a pharmaceutically acceptable salt of said ascorbic acid.

12. The composition of claim 1 comprising, per unit dose, 125–2000 mg of said norepinephrine precursor and 10–75 mg of said norepinephrine re-uptake inhibitor.

13. The composition of claim 7 comprising, per unit dose, 125–2000 mg of L-tyrosine and 10–75 mg of said norepinephrine re-uptake inhibitor.

14. The composition of claim 8 comprising, per unit dose, 10–75 mg of desipramine and 125–2000 mg of a norepinephrine precursor.

15. The composition of claim 5 comprising, per unit dose, 125–2000 mg of said norepinephrine precursor, 10–75 mg of said norepinephrine re-uptake inhibitor, 10–100 mg of pyridoxine, and 50–500 mg of ascorbic acid.

16. The composition of claim 15 wherein the said norepinephrine precursor is L-tyrosine and the said norepinephrine re-uptake inhibitor is desipramine.

17. A method for treating obesity, drug abuse, or narcolepsy in an animal comprising administering to said animal a composition comprising effective amounts of:
   a. a norepinephrine precursor; and
   b. a norepinephrine re-uptake inhibitor.

18. The method of claim 17 wherein said composition further comprises one or more enzymatic cofactors for the biosynthesis of norepinephrine 19. The method of claim 18 wherein said enzymatic cofactors include at least one of pyridoxine, ascorbic acid or the pharmaceutically acceptable salts thereof in an amount, effective to enzymatically cofactor biosynthesis of norepinephrine.

20. The method of claim 17 wherein said animal is a human.

21. The method of claims 17, 18, or 19 wherein said norepinephrine precursor is selected from the group of consisting of L-phenylalanine, L-tyrosine, and the pharmaceutically acceptable salts of L-phenylalanine and L-tyrosine, and said norepinephrine re-uptake inhibitor is selected from the group consisting of desipramine, imipramine, amoxapine, nortriptyline, protriptyline, and maprotiline, and the pharmaceutically acceptable salts of desipramine, imipramine, amoxapine, nortriptyline, protriptyline, and maprotiline.

22. The method of claim 17 wherein said composition comprises per part by weight of said norepinephrine re-uptake inhibitor or an equivalent amount of the pharmaceutically acceptable salt of said norepinephrine re-uptake inhibitor, 0.5–500 parts by weight of the norepinephrine precursor or an equivalent amount of the pharmaceutically acceptable salt thereof.

23. The method of claim 19 wherein said composition comprises, per part by weight of said norepinephrine re-uptake inhibitor or an equivalent amount of the pharmaceutically acceptable salt of said norepinephrine re-uptake inhibitor, 0.5–500 parts by weight of said norepinephrine precursor, 0.05–4 parts by weight of pyridoxine or an equivalent amount of a pharmaceutically acceptable salt of pyridoxine, and 0.4–20 parts by weight of said ascorbic acid or an equivalent amount of a pharmaceutically acceptable salt of said ascorbic acid.

24. The method of claim or 19 wherein said composition is administered to said animal one to eight times per day, each unit dose containing 125–2000 mg of said norepinephrine precursor or an equivalent amount of the pharmaceutically acceptable salt of said norepinephrine precursor, 10–75 mg of said norepinephrine re-uptake inhibitor or an equivalent amount of the pharmaceutically acceptable salt of said norepinephrine re-uptake inhibitor, 10–100 mg of said pyridoxine or an equivalent amount of the pharmaceutically acceptable salt of said pyridoxine, and 50–500 mg. of said ascorbic acid or an equivalent amount of the pharmaceutically acceptable salt of said ascorbic acid.

25. The method of claim 17, wherein said composition comprises, per unit dose, 1 gm L-tyrosine and 25 mg desipramine administered four times daily.

26. The method of claim 19, wherein said composition comprises, per unit dose, 1 gm L-tyrosine, 25 mg desipramine, 50 mg pyridoxine and 250 mg ascorbic acid.

27. The method of claim 17, wherein said composition further comprises a pharmaceutically acceptable carrier.

* * * * *